US012766022B2

(12) United States Patent
Roussel et al.

(10) Patent No.: US 12,766,022 B2
(45) Date of Patent: Oct. 20, 2026

(54) THUMB BRACE

(71) Applicant: DJO FRANCE, Mouguerre (FR)

(72) Inventors: Anaïs Roussel, Lahonce (FR); Beñat Sagardia, Saint-Pée-sur-Nivelle (FR)

(73) Assignee: DJO France, Mouguerre (FR)

( * ) Notice: Subject to any disclaimer, the term of this patent is extended or adjusted under 35 U.S.C. 154(b) by 0 days.

(21) Appl. No.: 18/981,229

(22) Filed: Dec. 13, 2024

(65) Prior Publication Data

US 2025/0177179 A1 Jun. 5, 2025

Related U.S. Application Data

(63) Continuation of application No. 17/178,786, filed on Feb. 18, 2021, now abandoned, which is a (Continued)

(51) Int. Cl.
*A61F 5/01* (2006.01)
*A61F 5/058* (2006.01)

(52) U.S. Cl.
CPC .................................. *A61F 5/0118* (2013.01)

(58) Field of Classification Search
CPC ...... A61F 5/00; A61F 5/01; A61F 5/05; A61F 5/10; A61F 5/0102; A61F 5/0104;
(Continued)

(56) References Cited

U.S. PATENT DOCUMENTS 3,209,750 A 10/1965 Levitt
4,665,907 A * 5/1987 Leverette .................. A61F 5/10 128/880
(Continued)

FOREIGN PATENT DOCUMENTS

DE 19511116 A1 9/1996
DE 202014007828 U1 11/2014
(Continued)

OTHER PUBLICATIONS

American Society for Surgery of the Hand: Dec. 1, 2016.*
(Continued)

*Primary Examiner* — Alireza Nia
*Assistant Examiner* — Andrew Jun-Wai Mok
(74) *Attorney, Agent, or Firm* — Veros Legal Solutions, LLP

(57) ABSTRACT

A thumb brace for at least partially immobilizing a thumb of a user is provided. The thumb brace includes a first curved support element configured to be disposed on a heel of a hand along an intercarpal articulation of the thumb and in a palmar gutter of the hand. The thumb brace includes a second curved support element coupled to the first curved support element and configured to be disposed on a palm of the hand along a metacarpophalangeal joint of the thumb. The thumb brace includes a third curved support element configured to be disposed on a backside of the hand along the intercarpal articulation of the thumb. The thumb brace includes a fourth curved support element coupled to the third curved support element and configured to be disposed on the backside of the hand along the metacarpophalangeal joint of the thumb. Related methods are also provided.

17 Claims, 5 Drawing Sheets

Related U.S. Application Data continuation of application No. PCT/US2019/043441, filed on Jul. 25, 2019.

(60) Provisional application No. 62/725,945, filed on Aug. 31, 2018.

(58) Field of Classification Search
CPC .......... A61F 5/0118; A61F 5/013; A61F 5/04; A61F 5/058; A61F 5/05825; A61F 5/05841; A61F 5/05858; A61F 5/05866; A61F 5/05875; A61F 2005/0181; A61F 2005/0186; A63B 71/14; A41D 19/01547; A41D 19/01564; A41D 19/01582; A41D 19/01588; A41D 13/08; A41D 13/081; A41D 13/082; A41D 13/084; A41D 13/087
See application file for complete search history.

(56) References Cited

U.S. PATENT DOCUMENTS

| | | | |
|---|---|---|---|
| 5,899,870 | A | 5/1999 | Deirmendjian et al. |
| 6,325,772 | B1 | 12/2001 | Scheuermann et al. |
| 2003/0191421 | A1 | 10/2003 | Weaver, II et al. |
| 2006/0026733 | A1* | 2/2006 | Nordt ..................... A41D 13/08 2/69 |
| 2015/0157483 | A1 | 6/2015 | Grunden et al. |
| 2017/0079831 | A1 | 3/2017 | Sayre |
| 2017/0348191 | A1 | 12/2017 | Salstein-Begley et al. |
| 2021/0169674 | A1 | 6/2021 | Roussel et al. |

FOREIGN PATENT DOCUMENTS

| | | | |
|---|---|---|---|
| EP | 0143348 | A1 | 6/1985 |
| EP | 1905399 | A1 | 4/2008 |
| NL | 2016047 | | 11/2018 |
| WO | 2002094140 | A2 | 11/2002 |
| WO | 2007066367 | A2 | 6/2007 |
| WO | 2007066367 | A3 | 8/2007 |
| WO | 2013160478 | A1 | 10/2013 |
| WO | 2014148906 | A1 | 9/2014 |
| WO | 2018044023 | A1 | 3/2018 |

OTHER PUBLICATIONS

Saint Luke's Health System: May 11, 2016.*

FLA® 3D Adjustable Thumb Brace, Atlantic Healthcare Products, viewed Apr. 25, 2025; https://www.atlantichp.com/fla-adjustable-3d-thumb-brace.html?srsltid=AfmBOoq14HKq80Ej9fqmAP7JFWGiqsb0M6oNJRsweUXDcakSMe6XWMJm.

importitall.co.za, Trigger Finger Splint for Alleviating Finger Locking, Straightening Curved, Bent, Locked & Stenosing Tenosynovitis, Best Finger Support Brace for Tendon Release & Pain Relief, Accessed May 2, 2018, https://www.importitall.co.za/Trigger-Finger-Splint-for-Alleviating-Finger-Locking-Straightening-Curved-Bent-Locked--Stenosing-Tenosynovitis-ap-B073PYPYQB.html.

Jo Southall, Rhizomed Thumb Support from Medi, JB Occupational Therapy; Sep. 13, 2014, United States, https://jboccupationaltherapy.co.uk/rhizomed-thumb-support/.

rehab-store.com, 3pp Thumbduction Strap, Accessed May 2, 2018, https://www.rehab-store.com/p-3pp-thumduction-strap.html, United States.

* cited by examiner

THUMB BRACE

CROSS-REFERENCE TO RELATED APPLICATIONS

This application is a continuation of and claims priority to U.S. patent application Ser. No. 17/178,786, filed on Feb. 18, 2021, which is a continuation of and claims priority to International PCT Application No. PCT/US2019/043441, filed on Jul. 25, 2019, which claims priority to U.S. Provisional Application Ser. No. 62/725,945, filed on Aug. 31, 2018. The contents of each aforementioned patent application are hereby incorporated by reference in their entireties.

FIELD OF THE DISCLOSURE

The present disclosure relates to braces for immobilizing an appendage of a user. Specifically, the apparatuses and methods described herein provide a thumb brace for at least partially immobilizing a thumb of the user.

DESCRIPTION OF RELATED TECHNOLOGY

Thumb braces have been used in the past to partially or fully immobilize a thumb of a hand of a user in treating or avoiding any number of injuries to the thumb, hand or particular joints of the same. However, conventional thumb braces may be bulky, uncomfortable or extend across a larger portion of the hand than desirable if the user wishes to retain as much use of the affected hand as possible.

Accordingly, there is a need for solutions that provide a less bulky, more comfortable and less intrusive brace that sufficiently supports, immobilizes and/or protects a thumb, hand, or particular joints of the same while maintaining a greater use of the affected hand.

SUMMARY

According to some embodiments, a thumb brace for at least partially immobilizing a thumb of a user is provided. The thumb brace includes a first curved support element configured to be disposed on a heel of a hand along an intercarpal articulation of the thumb and in a palmar gutter of the hand. The thumb brace includes a second curved support element coupled to the first curved support element and configured to be disposed on a palm of the hand along a metacarpophalangeal joint of the thumb. The thumb brace includes a third curved support element configured to be disposed on a backside of the hand along the intercarpal articulation of the thumb. The thumb brace includes a fourth curved support element coupled to the third curved support element and configured to be disposed on the backside of the hand along the metacarpophalangeal joint of the thumb.

According to some other embodiments, a method of using a thumb brace for at least partially immobilizing a thumb of a user is provided. The method includes disposing a first curved support element on a heel of a hand along an intercarpal articulation of the thumb and in a palmar gutter of the hand. The method includes disposing a second curved support element, coupled to the first curved support element, on a palm of the hand along a metacarpophalangeal joint of the thumb. The method includes disposing a third curved support element on a backside of the hand along the intercarpal articulation of the thumb. The method includes disposing a fourth curved support element, coupled to the third curved support element, on the backside of the hand along the metacarpophalangeal joint of the thumb.

According to some other embodiments, a method of manufacturing a thumb brace for at least partially immobilizing a thumb of a user is provided. The method includes forming a first curved support element configured to be disposed on a heel of a hand along an intercarpal articulation of the thumb and in a palmar gutter of the hand. The method includes forming a second curved support element coupled to the first curved support element and configured to be disposed on a palm of the hand along a metacarpophalangeal joint of the thumb. The method includes forming a third curved support element configured to be disposed on a backside of the hand along the intercarpal articulation of the thumb. The method includes forming a fourth curved support element coupled to the third curved support element and configured to be disposed on the backside of the hand along the metacarpophalangeal joint of the thumb.

DETAILED DESCRIPTION

Various aspects of the novel braces and associated methods are described more fully hereinafter with reference to the accompanying drawings. However, the disclosure may contemplate many different forms of such braces and associated methods and should not be construed as limited to any specific structure or function presented throughout this disclosure. Rather, these aspects are provided so that this disclosure will be thorough and complete, and will fully convey the scope of the disclosure to those skilled in the art. Based on the teachings herein one skilled in the art should appreciate that the scope of the disclosure is intended to cover any aspect of the novel braces and methods disclosed herein, whether implemented independently of or combined with any other aspect of the disclosure. For example, a brace may be implemented, or a method may be practiced using any number of the aspects set forth herein. In addition, the scope of the disclosure is intended to cover such a brace or method which is practiced using other structure, functionality, or structure and functionality in addition to or other than the various aspects of the disclosure set forth herein. It should be understood that any aspect disclosed herein may be embodied by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different applications, some of which are illustrated by way of example in the figures and in the following description of the preferred aspects. The detailed description and drawings are merely illustrative of the disclosure rather than limiting, the scope of the disclosure being defined by the appended claims and equivalents thereof.

Figure 1:
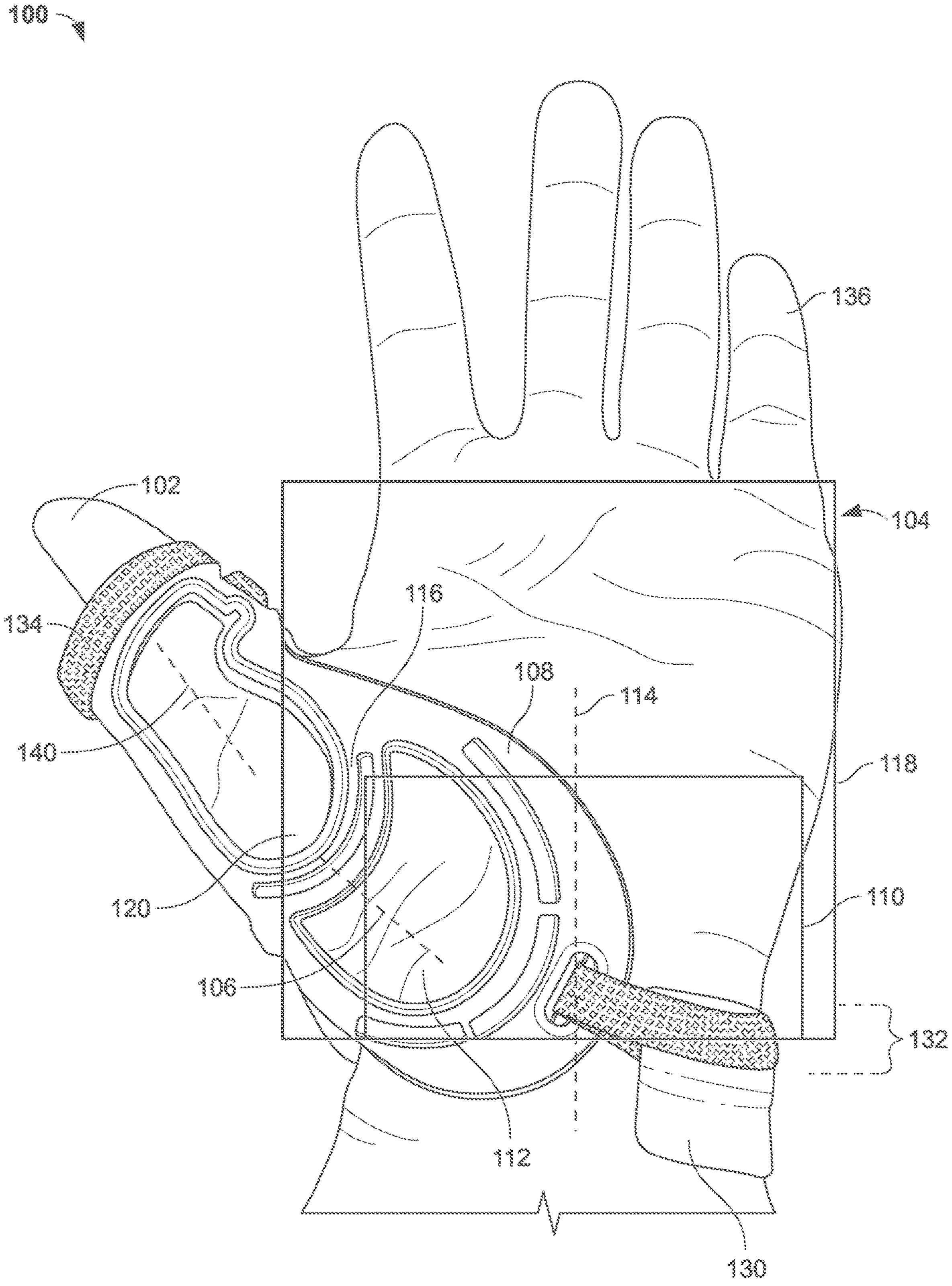
FIG. 1 illustrates a palm-side view of at least a portion of a thumb brace for at least partially immobilizing a thumb of a user, according to some embodiments.
Figure 2:
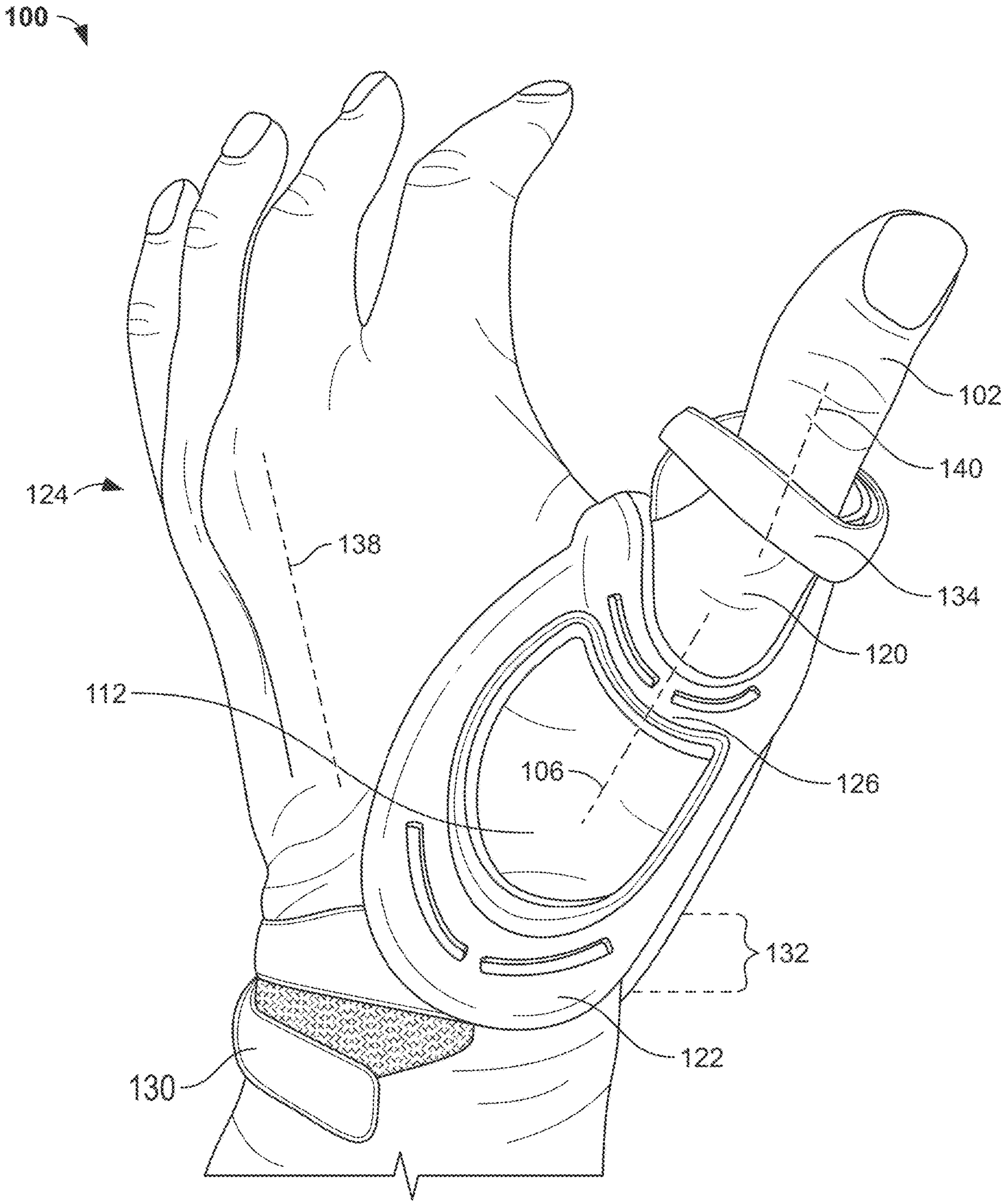
FIG. 2 illustrates a back-side view of at least a portion of the thumb brace of FIG. 1, according to some embodiments.
Figure 3:
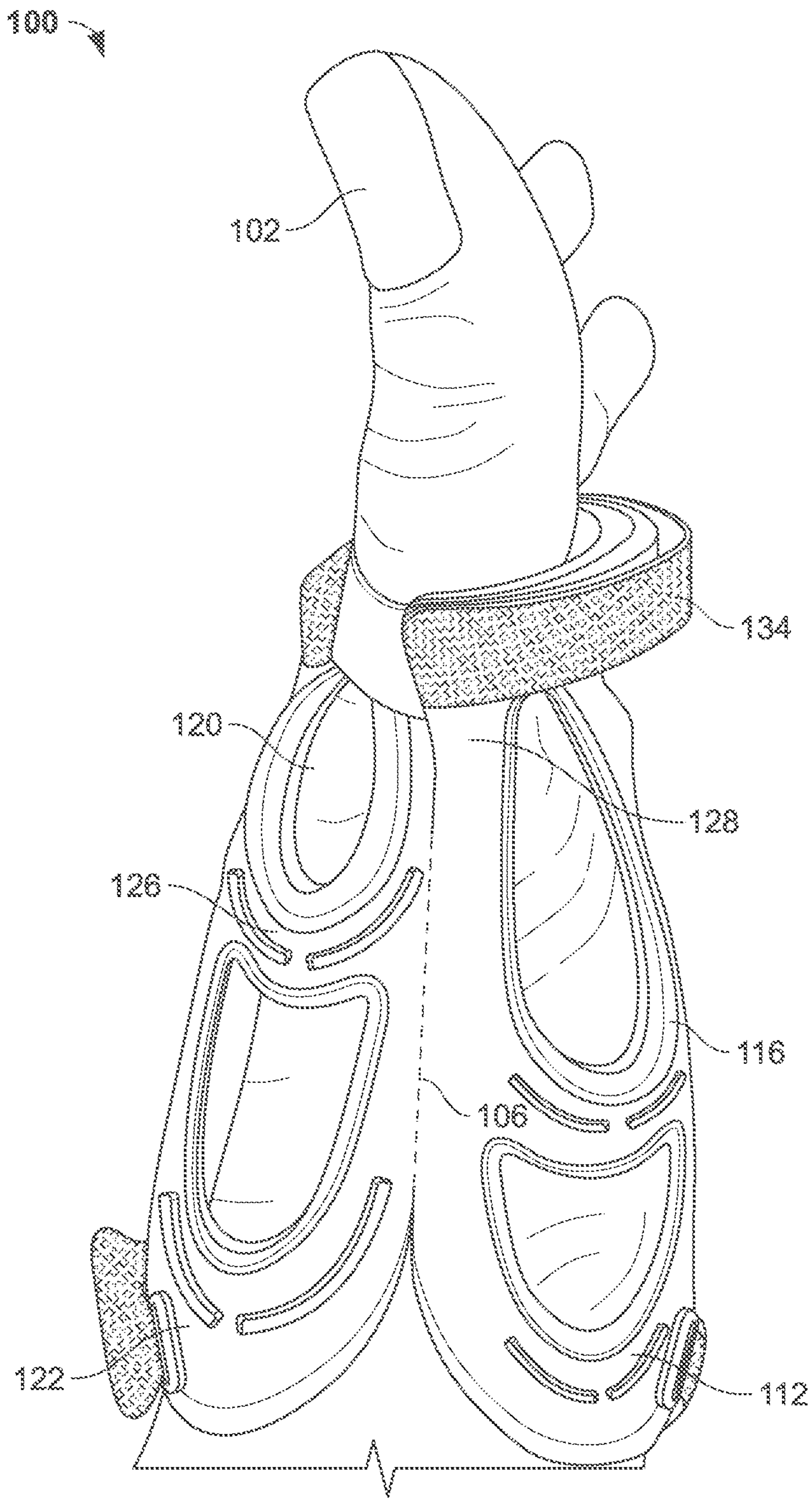
FIG. 3 illustrates a view of at least a portion of the thumb brace of FIGS. 1 and 2 along a side of the hand defined by a thumb metacarpal of the hand, according to some embodiments.

Several aspects of a thumb brace for at least partially immobilizing a thumb of a user will now be described in connection with FIGS. 1-3 together below. FIG. 1 illustrates a palm-side view of at least a portion of a thumb brace 100 for at least partially immobilizing a thumb 102 of a user, according to some embodiments. FIG. 2 illustrates a back-side view of at least a portion of thumb brace 100 of FIG. 1, according to some embodiments. FIG. 3 illustrates a view of at least a portion of thumb brace 100 of FIGS. 1 and 2 along a side of a hand 104 defined by a thumb metacarpal 106 of hand 104, according to some embodiments.

Thumb brace 100 comprises a first curved support element 108 configured to be disposed on a heel 110 of hand 104 along an intercarpal articulation 112 of thumb 102 and in a palmar gutter 114 of hand 104. First curved support element 108 secures thumb brace 100 within palmar gutter 114 and substantially surrounds at least a proximal portion of a thumb metacarpal 140 on a palm 118 and/or heel 110 of hand 104. Disposing first curved support element 108 along intercarpal articulation 112 of thumb 102 and in palmar gutter 114 of hand 104 ensures first curved support element 108 does not move substantially with respect to hand 104 once secured.

Thumb brace 100 comprises a second curved support element 116 coupled to first curved support element 108 and configured to be disposed on palm 118 of hand 104 along a metacarpophalangeal joint 120 of thumb 102. Second curved support element 116 substantially surrounds at least a proximal portion of metacarpophalangeal joint 120 of thumb 102 on palm 118 of hand 104 between a thumb phalange 106 and thumb metacarpal 140. Disposing second curved support element 116 on palm 118 of hand 104 along a metacarpophalangeal joint 120 of thumb 102 ensures second curved support element 116 secures thumb phalange 106 at substantially it's most distal extent, thereby providing a greater amount of leverage in preventing thumb 102 from substantially moving with respect to the rest of hand 104 once secured.

As seen best with reference to FIG. 2, thumb brace 100 comprises a third curved support element 122 configured to be disposed on a backside 124 of hand 104 along intercarpal articulation 112 of thumb 102. Third curved support element 122 substantially surrounds a proximal portion of intercarpal articulation 112 of thumb 102 along a backside and/or side of a wrist 132 of hand 104. Disposing third curved support element 122 to substantially surround the proximal portion of intercarpal articulation 112 of thumb 102 along the backside and/or side of wrist 132 of hand 104 ensures third curved support element 122 secures thumb phalange 106 at substantially it's most proximal extent.

Thumb brace 100 comprises a fourth curved support element 126 coupled to third curved support element 122 and configured to be disposed on backside 124 of hand 104 along metacarpophalangeal joint 120 of thumb 102. Fourth curved support element 126 substantially surrounds at least a proximal portion of metacarpophalangeal joint 120 of thumb 102 on backside 124 of hand 104 between thumb phalange 106 and thumb metacarpal 140. Disposing fourth curved support element 126 on backside 124 of hand 104 along metacarpophalangeal joint 120 of thumb 102 ensures fourth curved support element 126 secures thumb phalange 106 at substantially it's most distal extent, thereby providing a greater amount of leverage in preventing thumb 102 from substantially moving with respect to the rest of hand 104 once secured.

In some embodiments, first curved support element 108, second curved support element 116, third curved support element 122, and fourth curved support element 126 may each have a concave curvature that corresponds to a respective local curvature of a portion of hand 104 on which that element is configured to contact, thereby allowing each element 108, 116, 122, 126 to seat securely against respective portions of hand 104 and/or thumb 102.

In some embodiments, one or more of first curved support element 108, second curved support element 116, third curved support element 122, and fourth curved support element 126 may comprise respective strips of an elastomeric material or a fabric reinforced, internally or externally, with a semi-rigid material, such as metal, for example, aluminum. However, the present disclosure is not so limited and first curved support element 108, second curved support element 116, third curved support element 122, and fourth curved support element 126 may comprise any suitable material and may be reinforced internally, externally, or both with any suitable semi-rigid or rigid material, such as but not limited to plastic, ceramic, or acrylic materials.

Thumb brace 100 comprises a joining element 128 coupling first curved support element 108, second curved support element 116, third curved support element 122, and fourth curved support element 126 along a side of hand 104 defined by thumb metacarpal 106 of hand 104. Joining element 128 allows first curved support element 108 and second curved support element 116 to align properly on palm 118 and thumb 102 of the hand, and third curved support element 122 and fourth curved support element 126 to align properly on backside 124 and thumb 102 of hand 104. Moreover, joining element 128 ensures that none of first curved support element 108, second curved support element 116, third curved support element 122, and fourth curved support element 126 wrap around thumb 102 from palm 118 to backside 124 of hand 104. As shown in FIGS. 1-3, first curved support element 108 does not extend laterally toward a digitus minimus manus (hereinafter, "little finger") 136 of hand 104 substantially beyond palmar gutter 114. Similarly, third curved support element 122 does not extend laterally toward little finger 136 of hand 104 substantially beyond a midline 138 of backside 124 of hand 104. Accordingly, thumb brace 100 does not unnecessarily contact portions of hand 104 that would prevent, hinder or complicate use of hand 104 in ways that do not require substantial movement of thumb 102 with respect to hand 104. In some embodiments, two or more of joining element 128, first curved support element 108, second curved support element 116, third curved support element 122, and fourth curved support element 126 may be formed as a single or unitary piece.

Thumb brace 100 comprises a first strap 130 coupled to first curved support element 108 and configured to wrap around wrist 132 of hand 104 and couple to third curved support element 122. First strap 130 secures thumb brace 100, and specifically first and third curved support elements 108, 122 and joining element 128 against respective portions of hand 104. Thumb brace 100 comprises a second strap 134 coupled to joining element 128 and configured to wrap around thumb 102 and couple to at least one of second and fourth curved support elements 116, 126. Second strap 134 secures thumb brace 100, and specifically joining element 128 and so second and fourth curved support elements 116, 126 against respective portions of hand 104 and/or thumb 102. By disposing second strap 134 such that it secures to and/or around thumb 102, thumb 102 is secured at a position distal of metacarpophalangeal joint 120 of thumb 102, thereby ensuring substantially immobility of thumb 102 with respect to hand 102.

First strap 130 and second strap 134 may comprise fabric, leather, plastic, or any other suitable material having sufficient strength and durability to secure portions of thumb brace 100 as described above. In some embodiments, first strap 130 and second strap 134 may comprise hook and loop fasteners, buttons, snaps, pins or any other suitable type of fastener.

Figure 4:
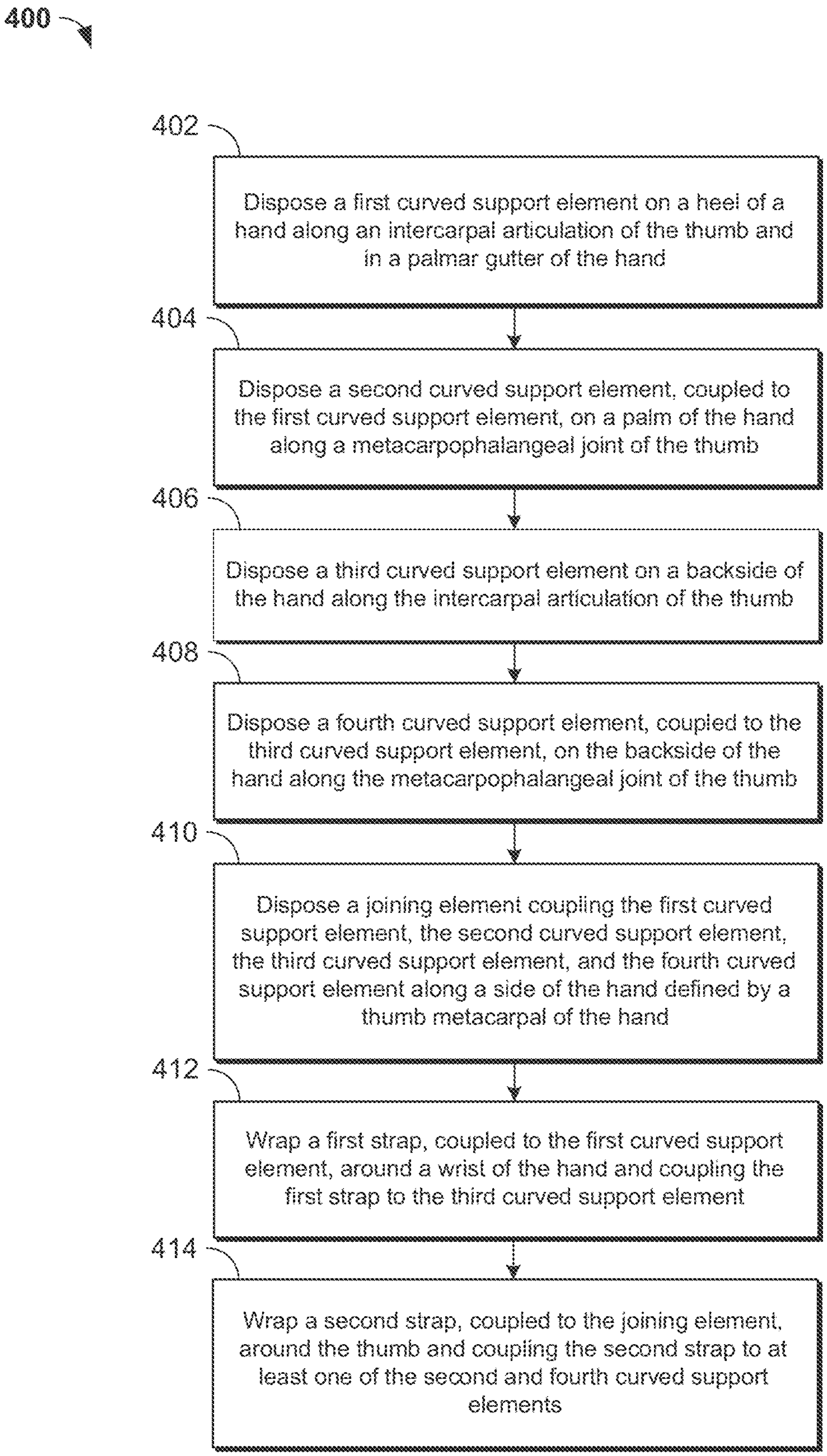
FIG. 4 illustrates a flowchart of a method for using a thumb brace for at least partially immobilizing a thumb of a user, according to some embodiments.

FIG. 4 illustrates a flowchart 400 of a method for using a thumb brace for at least partially immobilizing a thumb of a user, according to some embodiments. Flowchart 400 will now be described in connection with thumb brace 100 as previously described in connection with FIGS. 1-3 above.

Block 402 includes disposing a first curved support element on a heel of a hand along an intercarpal articulation of a thumb and in a palmar gutter of the hand. For example, as previously described in connection with FIGS. 1-3, first curved support element 108 may be configured to be disposed on heel 110 of hand 104 along intercarpal articulation 112 of thumb 102 and in palmar gutter 114 of hand 104.

Block 404 includes disposing a second curved support element, coupled to the first curved support element, on a palm of the hand along a metacarpophalangeal joint of the thumb. For example, as previously described in connection with FIGS. 1-3, second curved support element 116 may be coupled to first curved support element 108 and may be configured to be disposed on palm 118 of hand 104 along metacarpophalangeal joint 120 of thumb 102.

Block 406 includes disposing a third curved support element on a backside of the hand along the intercarpal articulation of the thumb. For example, as previously described in connection with FIGS. 1-3, third curved support element 122 may be configured to be disposed on backside 124 of hand 104 along intercarpal articulation 112 of thumb 102.

Block 408 includes disposing a fourth curved support element, coupled to the third curved support element, on the backside of the hand along the metacarpophalangeal joint of the thumb. For example, as previously described in connection with FIGS. 1-3, fourth curved support element 126 may be coupled to third curved support element 122 and configured to be disposed on backside 124 of hand 104 along metacarpophalangeal joint 120 of thumb 102.

Block 410 includes disposing a joining element coupling the first curved support element, the second curved support element, the third curved support element, and the fourth curved support element along a side of the hand defined by a thumb metacarpal of the hand. For example, as previously described in connection with FIGS. 1-3, joining element 128 may be disposed to couple first curved support element 108, second curved support element 116, third curved support element 122, and fourth curved support element 126 along a side of hand 104 defined by thumb metacarpal 106 of hand 104.

Block 412 includes wrapping a first strap, coupled to the first curved support element, around a wrist of the hand and coupling the first strap to the third curved support element. For example, as previously described in connection with FIGS. 1-3, first strap 130 may be coupled to first curved support element 108 and first strap 130 may be configured to wrap around wrist 132 of hand 104 and couple to third curved support element 122.

Block 414 includes wrapping a second strap, coupled to the joining element, around the thumb and coupling the second strap to at least one of the second and fourth curved support elements. For example, as previously described in connection with FIGS. 1-3, second strap 134 may be coupled to joining element 128 and second strap 134 may be configured to wrap around thumb 102 and may be coupled to at least one of second and fourth curved support elements 116, 126.

Figure 5:
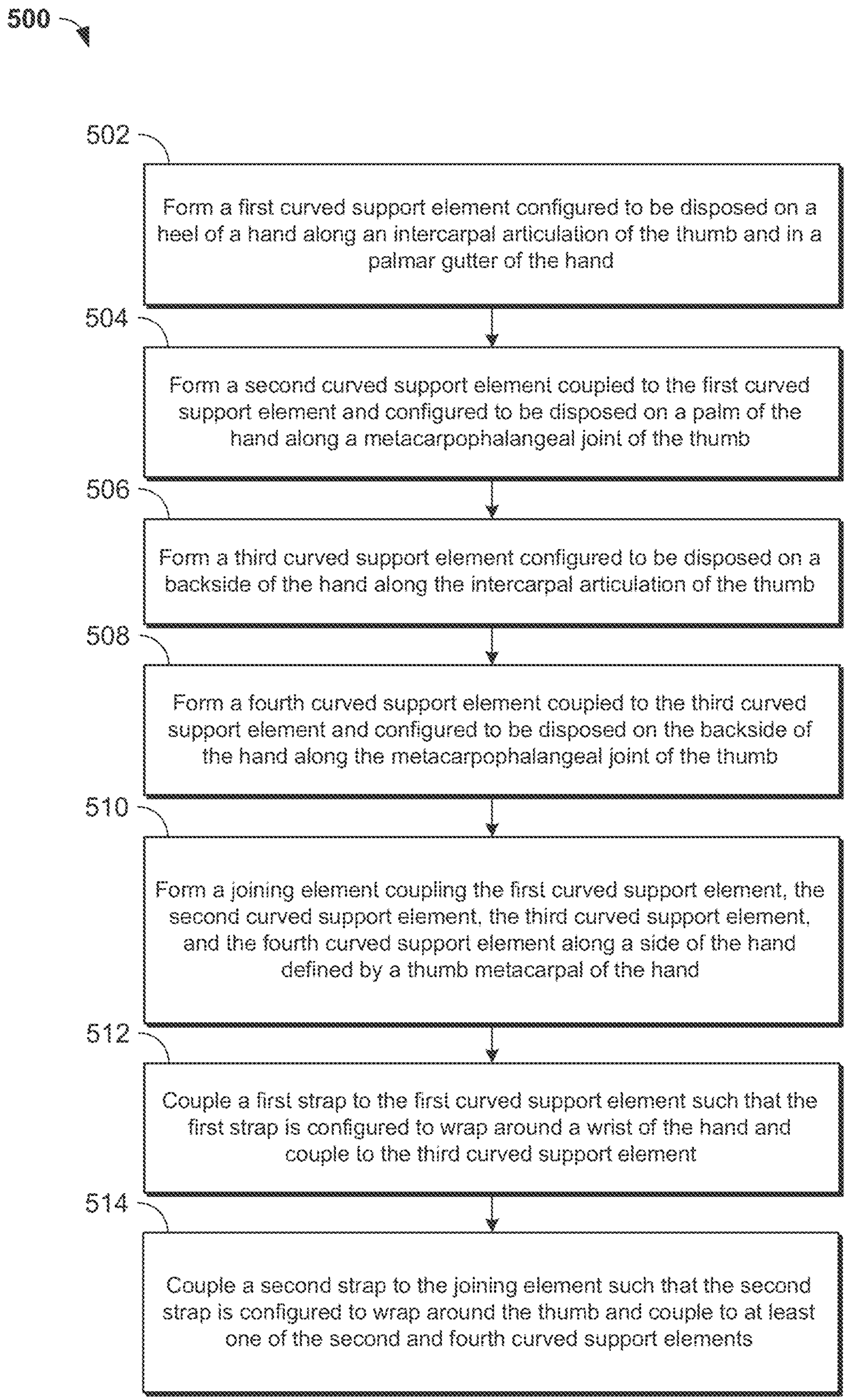
FIG. 5 illustrates a flowchart of a method for manufacturing a thumb brace for at least partially immobilizing a thumb of a user, according to some embodiments.

FIG. 5 illustrates a flowchart 500 of a method for manufacturing a thumb brace for at least partially immobilizing a thumb of a user, according to some embodiments. Flowchart 500 will now be described in connection with thumb brace 100 as previously described in connection with FIGS. 1-3 above.

Block 502 includes forming a first curved support element configured to be disposed on a heel of a hand along an intercarpal articulation of the thumb and in a palmar gutter of the hand. For example, as previously described in connection with FIGS. 1-3, upon proper formation, first curved support element 108 may be configured to be disposed on heel 110 of hand 104 along intercarpal articulation 112 of thumb 102 and in palmar gutter 114 of hand 104.

Block 504 includes forming a second curved support element coupled to the first curved support element and configured to be disposed on a palm of the hand along a metacarpophalangeal joint of the thumb. For example, as previously described in connection with FIGS. 1-3, upon proper formation, second curved support element 116 may be coupled to first curved support element 108 and may be configured to be disposed on palm 118 of hand 104 along metacarpophalangeal joint 120 of thumb 102.

Block 506 includes forming a third curved support element configured to be disposed on a backside of the hand along the intercarpal articulation of the thumb. For example, as previously described in connection with FIGS. 1-3, upon proper formation, third curved support element 122 may be configured to be disposed on backside 124 of hand 104 along intercarpal articulation 112 of thumb 102.

Block 508 includes forming a fourth curved support element coupled to the third curved support element and configured to be disposed on the backside of the hand along the metacarpophalangeal joint of the thumb. For example, as previously described in connection with FIGS. 1-3, upon proper formation, fourth curved support element 126 may be coupled to third curved support element 122 and may be configured to be disposed on backside 124 of hand 104 along metacarpophalangeal joint 120 of thumb 102.

Block 510 includes forming a joining element coupling the first curved support element, the second curved support element, the third curved support element, and the fourth curved support element along a side of the hand defined by a thumb metacarpal of the hand. For example, as previously described in connection with FIGS. 1-3, upon proper formation, joining element 128 may couple first curved support element 108, second curved support element 116, third curved support element 122, and fourth curved support element 126 along a side of hand 104 defined by thumb metacarpal 106 of hand 104.

Block 512 includes coupling a first strap to the first curved support element such that the first strap is configured to wrap around a wrist of the hand and couple to the third curved support element. For example, as previously described in connection with FIGS. 1-3, upon proper coupling, first strap 130 may be coupled to first curved support element 108 and first strap 130 may be configured to wrap around wrist 132 of hand 104 and couple to third curved support element 122.

Block 514 includes coupling a second strap to the joining element such that the second strap is configured to wrap around the thumb and couple to at least one of the second and fourth curved support elements. For example, as previously described in connection with FIGS. 1-3, upon proper coupling, second strap 134 may be coupled to joining element 128 and second strap 134 may be configured to wrap around thumb 102 and may be coupled to at least one of second and fourth curved support elements 116, 126.

Various modifications to the implementations described in this disclosure can be readily apparent to those skilled in the art, and any generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that may be described in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

In addition, the methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

While the foregoing is directed to aspects of the present disclosure, other and further aspects of the disclosure may be devised without departing from the basic scope thereof, and the scope thereof is determined by the claims that follow.

The invention claimed is:

1. A thumb brace for at least partially immobilizing a thumb of a hand of a user, comprising:

a first curved support element configured to be disposed along an intercarpal articulation of the thumb;

a second curved support element directly coupled to the first curved support element and configured to extend along a metacarpophalangeal joint of the thumb;

a third curved support element configured to be disposed along the intercarpal articulation of the thumb on a backside of a hand along the intercarpal articulation of the thumb;

a fourth curved support element directly coupled to the third curved support element and configured to be disposed on the backside of the hand along the metacarpophalangeal joint of the thumb; and a joining element configured to be disposed along a side of the hand defined by a thumb metacarpal of the hand, each of the first curved support element, the second curved support element, the third curved support element, and the fourth curved support element directly coupled to and extending from the joining element along the side of the hand, wherein the second curved support element is directly coupled to the fourth curved support element forming a permanently closed loop configured to encircle the metacarpophalangeal joint of the thumb.

2. The thumb brace of claim 1, wherein one or more of the first curved support element, the second curved support element, the third curved support element, and the fourth curved support element has a concave curvature.

3. The thumb brace of claim 2, wherein the concave curvature corresponds to a respective local curvature of a portion of the hand on which at least one of the one or more of the first, second, third and fourth curved support elements is configured to contact.

4. The thumb brace of claim 1, further comprising a first strap coupled to the first curved support element, the first strap configured to wrap around a wrist of the hand and couple to the third curved support element.

5. The thumb brace of claim 1, further comprising a second strap coupled to the joining element, the second strap configured to wrap around the thumb and coupled to at least one of the second and fourth curved support elements.

6. The thumb brace of claim 1, wherein the first curved support element is not configured to extend laterally toward a digitus minimus manus of the hand.

7. The thumb brace of claim 1, wherein the third curved support element is configured not to extend laterally toward a digitus minimus manus of the hand beyond a midline of the hand.

8. The thumb brace of claim 1, wherein the first curved support element is configured to surround at least a proximal portion of a thumb metacarpal on the palm and/or the heel of the hand.

9. The thumb brace of claim 1, wherein second curved support element is configured to surround at least a proximal portion of the metacarpophalangeal joint of the thumb on the palm of the hand between a thumb phalange and a thumb metacarpal.

10. The thumb brace of claim 1, wherein the third curved support element is configured to surround a proximal portion of the intercarpal articulation of the thumb along a backside and/or a side of a wrist of the hand.

11. The thumb brace of claim 1, wherein the fourth curved support element is configured to surround at least a proximal portion of the metacarpophalangeal joint of the thumb on the backside of the hand between a thumb phalange and a thumb metacarpal.

12. The thumb brace of claim 1, wherein the first, second, third and fourth curved support elements comprise at least one of an elastomeric material or a fabric reinforced with a semi-rigid material.

13. The thumb brace of claim 1, wherein none of the first, second, third or fourth curved support elements are configured to wrap around the thumb from the palm to the backside of the hand.

14. A method of using a thumb brace for at least partially immobilizing a thumb of a user, the method comprising:

disposing a joining element of the thumb brace along a side of a hand defined by a metacarpal of the thumb;

disposing a first curved support element of the thumb brace on a heel of a hand along an intercarpal articulation of the thumb and in a palmar gutter of the hand;

disposing a second curved support element of the thumb brace, directly coupled to the first curved support element, on a palm of the hand along a metacarpophalangeal joint of the thumb;

disposing a third curved support element of the thumb brace on a backside of the hand along the intercarpal articulation of the thumb; and disposing a fourth curved support element of the thumb brace, directly coupled to the third curved support element, on the backside of the hand along the metacarpophalangeal joint of the thumb, wherein:

each of the first curved support element, the second curved support element, the third curved support element, and the fourth curved support element directly couple to and extend from the joining element, and the second curved support element is directly coupled to the fourth curved support element forming a permanently closed loop configured to encircle the metacarpophalangeal joint of the thumb.

15. The method of claim 14, further comprising at least one of:

wrapping a first strap, coupled to the first curved support element, around a wrist of the hand and coupling the first strap to the third curved support element; and wrapping a second strap, coupled to the joining element, around the thumb and coupling the second strap to at least one of the second and fourth curved support elements.

16. A method of manufacturing a thumb brace for at least partially immobilizing a thumb of a hand of a user, the method comprising:

forming a joining element of the thumb brace configured to be disposed along a side of the hand defined by a thumb metacarpal of the hand;

forming a first curved support element of the thumb brace configured to be disposed on a heel of a hand along an intercarpal articulation of the thumb and in a palmar gutter on the heel of the hand;

forming a second curved support element of the thumb brace directly coupled to the first curved support element and configured to be disposed on a palm of the hand along a metacarpophalangeal joint of the thumb;

forming a third curved support element of the thumb brace configured to be disposed on a backside of the hand along the intercarpal articulation of the thumb; and forming a fourth curved support element of the thumb brace directly coupled to the third curved support element and configured to be disposed on the backside of the hand along the metacarpophalangeal joint of the thumb, wherein:

each of the first curved support element, the second curved support element, the third curved support element, and the fourth curved support element directly couple to and extend from the joining element, and the second curved support element is directly coupled to the fourth curved support element forming a permanently closed loop configured to encircle the metacarpophalangeal joint of the thumb.

17. The method of claim 16, further comprising at least one of:

coupling a first strap of the thumb brace to the first curved support element such that the first strap is configured to wrap around a wrist of the hand and couple to the third curved support element; and coupling a second strap of the thumb brace to the joining element such that the second strap is configured to wrap around the thumb and couple to at least one of the second and fourth curved support elements.

* * * * *